US007435253B1

(12) United States Patent
Hartley et al.

(10) Patent No.: US 7,435,253 B1
(45) Date of Patent: Oct. 14, 2008

(54) PROSTHESIS AND A METHOD AND MEANS OF DEPLOYING A PROSTHESIS

(75) Inventors: David Hartley, Subiaco (AU); Michael Lawrence-Brown, Floreat (AU)

(73) Assignee: William A. Cook Australia Pty Ltd, Brisbane, Queensland (AU)

( * ) Notice: Subject to any disclaimer, the term of this patent is extended or adjusted under 35 U.S.C. 154(b) by 0 days.

(21) Appl. No.: 09/449,270

(22) Filed: Nov. 24, 1999

Related U.S. Application Data

(63) Continuation of application No. PCT/AU98/00383, filed on May 25, 1998.

(30) Foreign Application Priority Data

May 26, 1997 (AU) .................................... PO7008

(51) Int. Cl.
*A61F 2/06* (2006.01)

(52) U.S. Cl. ..................... 623/1.12; 623/1.11; 623/1.35

(58) Field of Classification Search ......... 623/1.1–1.35; 606/190–195
See application file for complete search history.

(56) References Cited

U.S. PATENT DOCUMENTS 5,122,154 A 6/1992 Rhodes
5,282,824 A 2/1994 Gianturco
5,387,235 A 2/1995 Chuter
5,415,664 A 5/1995 Pinchuk
5,534,007 A * 7/1996 St. Germain et al. ....... 623/1.11
5,562,724 A 10/1996 Vorwerk et al.
5,609,627 A * 3/1997 Goicoechea et al. ....... 623/1.35
5,628,783 A * 5/1997 Quiachon et al. ........... 606/194
5,634,941 A 6/1997 Winston et al.
5,693,083 A * 12/1997 Baker et al. ................. 606/195
5,957,973 A * 9/1999 Quiachon et al. ........... 606/194
5,961,548 A 10/1999 Shmulewitz
6,039,758 A 3/2000 Quiachon et al.
6,139,572 A * 10/2000 Campbell et al. .......... 623/1.11
6,346,118 B1 * 2/2002 Baker et al. ................ 623/1.12
6,352,553 B1 * 3/2002 van der Burg et al. ...... 623/1.23
6,562,063 B1 * 5/2003 Euteneuer et al. .......... 623/1.12

FOREIGN PATENT DOCUMENTS

EP 0461791 12/1991
EP 0637454 2/1995
EP 0684022 11/1995
EP 0712614 5/1996
EP 0795305 9/1997
FR 2722678 1/1996
WO 9624308 8/1996
WO 9633672 10/1996
WO 9638101 12/1996
WO 9807388 2/1998

* cited by examiner

*Primary Examiner*—Julian W Woo
(74) *Attorney, Agent, or Firm*—Richard J. Godlewski

(57) ABSTRACT

An introducer (1) adapted for the introduction of a self-expanding endovascular prosthesis (20) in a lumen of a patient. The introducer has attachment devices (10,30) to hold each end of the prosthesis so that each can be moved independently. An end ovascular prosthesis (20) is also claimed with stents at the proximal and distal ends being within the graft. The remainder of the stents are positioned on the outside of the graft body.

18 Claims, 17 Drawing Sheets

1 36 39 46 15 16 25 24 1 26 35 30 41 3 2 20 10 15 21 11

Figure 1:
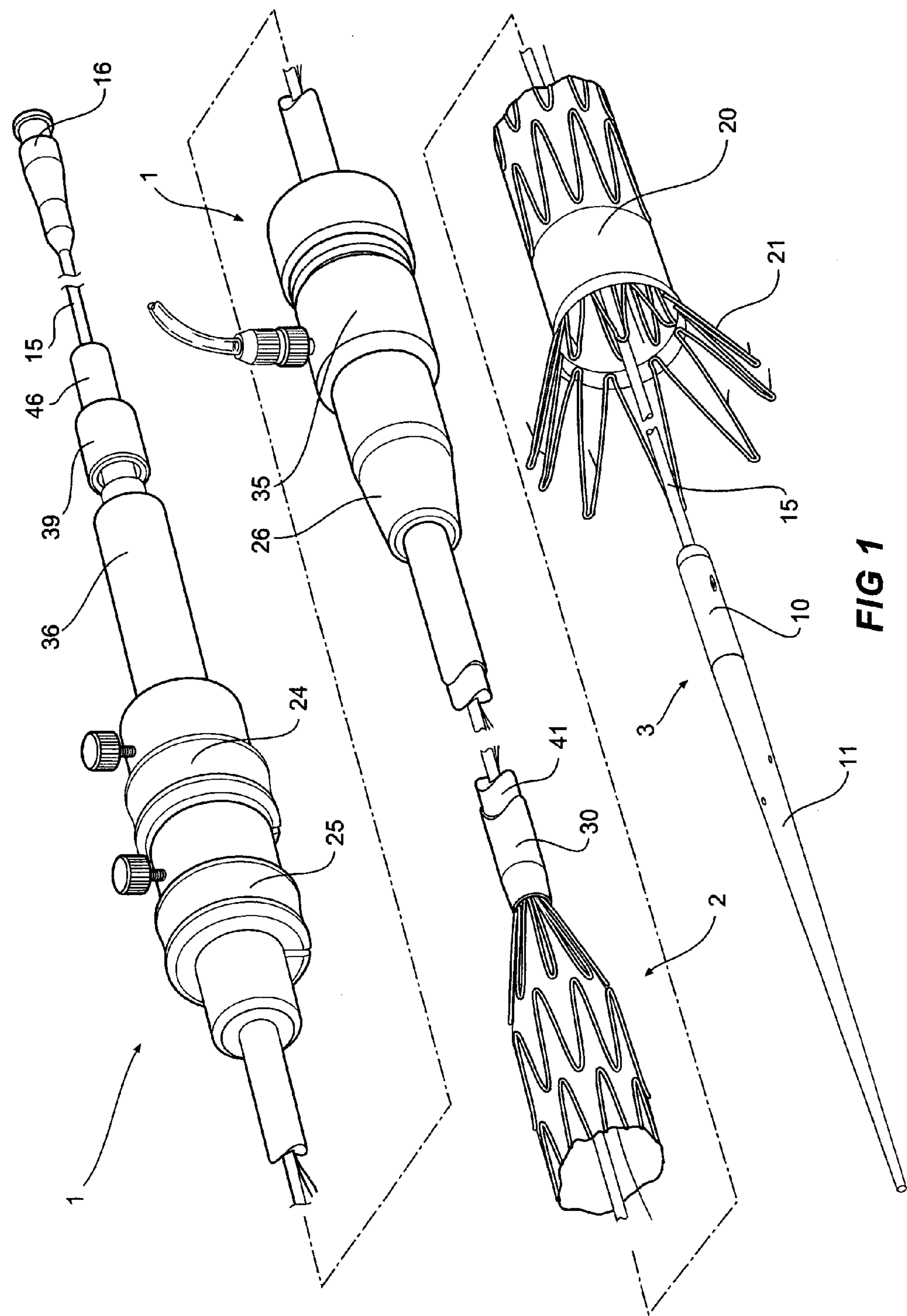

36
25
24
39
15
16
30
35
41
11
3
10
30
20

36
39
16
20
42
43
40
35
11
10

162
161
171
172
170
167
168
30□
160
163
165
166

175

161
160

41
36
15
38
44
25
37
22
24
37

73
70
80

75
79
71
78
77
79
71
60
71
74

PROSTHESIS AND A METHOD AND MEANS OF DEPLOYING A PROSTHESIS

CROSS REFERENCE TO RELATED COPENDING APPLICATION

This application is a continuation of International Application Number PCT/AU98/00383 filed May 25, 1998 and Australian Application Number PO 7008 filed May 26, 1997.

FIELD OF INVENTION

This invention relates to an method and means for introducing an expandable intraluminal prosthesis which may be straight, tubular or bifurcated in form and intended for the endovascular repair of diseased or damaged vessels and to a prosthesis which is suitable for such a procedure.

Throughout this specification the terms proximal and proximally are used for a position or direction towards the patient's heart and the terms distal and distally are used for a position or direction away the patient's heart.

BACKGROUND OF THE INVENTION

The deployment of intraluminal prostheses into the lumen of a patient from a remote location by the use of a deployment device or introducer, has been disclosed in a number of earlier patent specifications.

U.S. Pat. No. 4,562,596 in the name of Kornberg proposes the retention of a self expanding graft within a sleeve until it is to be deployed at which time the sleeve is withdrawn and the graft allowed to expand. After the graft has been released there is no possible control of the position of the distal end of the graft. Inadequate placement can render the entire deployment null and void.

U.S. Pat. No. 4,665,918 in the name of Garza et al proposes a system and method for the deployment of a prosthesis in a blood vessel. The prosthesis is positioned between a delivery catheter and an outer sheath and expands outwardly upon removal of the sheath. Once again after the prosthesis has been released by removal of the sheath there is no possible control of the position of the either end of the prosthesis.

U.S. Pat. No. 4,950,227 in the name of Savia et al proposes the delivery of a stent by mounting the stent to the outside of an inflatable catheter and retaining the ends of an unexpanded stent by fitting a sleeve over either end of the stent. Expansion of the stent is caused by inflation of the catheter between the sleeves so that the ends of the stent are withdrawn from the respective sleeves and the stent released and expanded into position. This system provides very little control over the deployment procedure and in practice would be impractical for intraluminal deployment where accuracy is vital.

European Patent specification No. 472 731 in the name of Inoue proposes an artificial tube prosthesis to be inserted into a human organ in a folded condition retained within a catheter and released to expand within the organ. Deployment is achieved by retention of the proximal end of the prosthesis by wires passing through a tube through the middle of the prosthesis while withdrawing the catheter. A balloon is then used to expand the prosthesis. Once again after the prosthesis has been released by removal of the catheter there is no possible control of the position of the distal end of the prosthesis.

U.S. Pat. No. 5,071,407 in the name of Termin et al proposes the delivery of a stent by retaining the stent in an elastically deformed condition between a catheter and a sheath. The proximal end of the stent is retained at the catheter. The stent is allowed to expand by removal of the sheath and optional balloon expansion. No indication is given of any method for release of the stent from the catheter or how the distal end of the stent can be positioned accurately.

Australian Patent Application No. 669,338 in the name of Chuter proposes a delivery arrangement for transluminally positioning a prosthesis at a particular position on an internal wall of a lumen. The delivery arrangement has an outer sheath to surround the prosthesis and a retention arrangement to hold the prosthesis in a selected position during removal of the sheath before final release.

Australian Patent Application No. 671,910 in the name of Endovascular Technologies, Inc. proposes a delivery arrangement for positioning a prosthesis within a lumen. It has capsules which retain each end of the prosthesis and a balloon arrangement to expand the prosthesis when the capsules have been retracted to release the prosthesis. A sheath is used to protect the prosthesis during insertion. Once the capsules have been withdrawn there is no method provided to ensure that the ends of the prosthesis are correctly positioned.

It is the object of this invention to provide a graft and a method and apparatus to deploy the graft prosthesis which will overcome at least some of the problems discussed above or at least provide an alternative arrangement to the prior art systems described above.

BRIEF DESCRIPTION OF THE INVENTION

According to one aspect of the present invention there is provided an introducer for positioning an expandable endovascular prosthesis in a lumen of a patient, the prosthesis having a proximal portion and a distal portion, the introducer comprising a prosthesis positioning mechanism selectively releasable from the prosthesis when the prosthesis is positioned at a desired site in the lumen of a patient, a first control member controlling at least the longitudinal position of the proximal portion of the prosthesis; and a second control member controlling at least the longitudinal position of the distal portion of the prosthesis. The prosthesis positioning mechanism can include a distal attachment region and/or a proximal attachment region. The distal attachment region can include a distal attachment device. The proximal attachment region can include a proximal attachment device. The prosthesis positioning mechanism can preferably include a control arrangement for controlling the length of the prosthesis. The prosthesis positioning mechanism can also preferably include a rotational arrangement by which the relative angular orientation of the proximal and distal portions of the prosthesis can be adjusted. This prosthesis positioning mechanism can singly or in combination also adjust the angular orientation of the prosthesis The introducer can also preferably comprise an expansion control mechanism for controlling expansion of the prosthesis when the prosthesis is positioned at the desired site in the lumen of the patient.

According to another aspect of the present invention there is provided provides an endovascular arrangement for positioning an expandable prosthesis at a desired location in a lumen of a patient, said arrangement comprising a control section to be maintained external to the patient, and a prosthesis positioning mechanism controllable by the control section for moving and manipulating the prosthesis to a desired location in the lumen, wherein a first member extends from the control section to a proximal region of the positioning mechanism, the proximal region of the positioning mechanism having means for controlling the proximal end of the prosthesis, wherein a second member extends from the control section to a distal region of the positioning mechanism, the distal region having means for controlling the distal end of the prosthesis in cooperation with the second member. The arrangement further preferably comprises contraction means for containing self-expanding stents of the prosthesis during insertion of the prosthesis positioning mechanism into the lumen and/or expansion means for expanding expandable stents of the prosthesis when the prosthesis is positioned at the desired site in the lumen of the patient. The contraction means preferably includes tubular means that extends from the control section to the positioning mechanism and serves to contain the prosthesis during insertion of the positioning mechanism into the lumen and to control the distal end of the prosthesis when the tubular means has been moved in a distal direction relative to the first and second members, relative movement between the first and second members enabling manipulation of the prosthesis when in the lumen. The expansion means includes at least radial means such as preferably an inflatable balloon for radially expandable stents of the prosthesis when the prosthesis is positioned at the desired location in the lumen. The first and second members can be contained within the said tubular means. Means can be provided for clamping the first and second members together during insertion of the prosthesis and for releasing the first and second members prior to the manipulation. Expansion of a non self expanding prosthesis can be performed by expansion of a balloon located around the first member and within the prosthesis, said balloon being inflatable from the control section. The proximal region of the attachment mechanism can contain tubular means for containing the proximal end of the prosthesis prior to final positioning thereof, and release of the prosthesis from the tubular means can be achieved by proximal movement of the first member. The second member has means for controlling the distal end of the stent whilst the latter is inside a tubular means. The arrangement can further comprise release mechanisms in the control section for controlling wires extending to respective stents of the prosthesis. The prosthesis positioning mechanism can preferably include a control arrangement for controlling the length of the prosthesis. The prosthesis positioning mechanism can also preferably include a rotational arrangement by which the relative angular orientation of the proximal and distal portions of the prosthesis can be adjusted. This prosthesis positioning mechanism can singly or in combination also adjust the angular orientation of the prosthesis. The introducer can also preferably comprise an expansion control mechanism for controlling expansion of the prosthesis when the prosthesis is positioned at the desired site in the lumen of the patient.

The above introducer and/or arrangement can be used to locate expandable prostheses or self-expandable prostheses. If the former are used, then one or more balloons, inflatable from a control section or external the patient, can be used.

The first member in the endovascular arrangement can either be fixed to an extension or the member can actually be shaped into the form of the extension.

The first and second control members of the introducer can singly or in combination preferably include a trigger wire positioned at the proximal and/or distal ends of the prosthesis. The trigger wire(s) can preferably extend to one or more release mechanisms external to patient for releasing the prosthesis from the positioning mechanism when the prosthesis is positioned at the lumen site in the patient.

Some form of container or expansion control mechanism can be used to contain that and while the remainder of the prosthesis is being manipulated in the lumen of the patient. It is after the manipulation has been executed that the container is removed by operation of the various control members.

In another aspect of the invention, the introducer or endovascular arrangement of the invention can also comprise a control arrangement for controlling the length of the prosthesis during the manipulation in the patient. In one aspect, the control arrangement or members can preferably include coaxial tubes which are connected to the respective ends of the prosthesis for rotation thereof. When the control members are locked together, the entire prosthesis can be rotated in the lumen of the patient. Alternatively, the control arrangement and/or members can be individually controlled for rotating the relative ends of the prosthesis with respect to each other in the same or opposite directions.

The sleeve can be independently located relative to the control arrangement and/or the first and second control members. The control arrangement or members can also be contained within the sleeve. The sleeve can preferably be a tube, wraps of wire, or a tube with wire therein. The aforementioned trigger or release wires can also be contained in the sleeve tube or in the wall of the tube.

With respect to an expandable prosthesis, the expansion means for expanding expandable stents of the prosthesis can preferably include one or more balloons (more preferably three balloons) for advantageously and independently expanding the proximal and distal portions of the prosthesis as well as the mid section thereof.

In an alternate form the invention may be said to reside in an introducer adapted for the introduction of a self expanding endovascular prosthesis into a lumen of a patient, the prosthesis having a proximal end and a distal end, the introducer comprising, a proximal attachment device adapted to be attached to the proximal end of the prosthesis, a distal attachment device adapted to be attached to the distal end of the prosthesis, each of the proximal and distal attachment devices attaching to the prosthesis in such a manner that the prosthesis can be held in tension therebetween and that each end of the prosthesis can be individually moved in proximal and distal directions and be rotated, and proximal releasing means associated with the proximal attachment device and distal releasing means associated with the distal attachment device to enable selective releasing of the proximal and distal ends of the prosthesis.

In a preferred form of the invention the proximal attachment means has a long tapering flexible extension on its proximal end to facilitate insertion of the introducer into a body lumen and its advancement along the lumen.

The proximal attachment device may be mounted on a flexible thin walled tube which extends in a distal direction from the proximal attachment device to an external manipulation section of the introducer which is adapted to remain external of the patient.

The thin walled metal tube may include fluid connection means external of the patient to enable the introduction of a medical reagent therethrough.

The long flexible extension may include a hollow tube therethrough in fluid communication with the thin walled metal tube and a plurality of side holes to enable dispersion of the medical reagent proximal of the prosthesis.

In a preferred form of the invention the distal attachment device is mounted on a flexible thick walled tubing and coaxial on the thin walled tube and extending in a distal direction to the external manipulation section and mounted such that the respective tubes can be moved together or independently.

There may be further included a haemostatic seal between the thin walled tube and the thick walled tube in the manipulation section.

There may be further included means to introduce a medical reagent into an annular space defined between the thin walled tube and the thick walled tube.

In a preferred form of the invention there may be a proximal trigger wire extending from the proximal attachment device to the manipulation section, the proximal trigger wire being adapted to activate the proximal releasing means and a distal trigger wire extending from the distal attachment device to the manipulation section, the distal trigger wire being adapted to activate the distal releasing means.

In a preferred form of the invention there may be included an external release mechanism for each of the proximal trigger wire and distal trigger wire, the external release mechanism adapted to prevent accidental release of the trigger wires and to allow release of the distal releasing means only after release of the proximal releasing means.

Preferably there is a haemostatic seal around the respective trigger wires in the manipulation section.

The introducer may also include an external sheath extending from external of the patient to cover and compress the prosthesis during insertion of the introducer into a patient and movable longitudinally from outside the patient to expose the prosthesis.

The external sheath may be coaxial with and in a sliding fit on the thick walled tube. The external sheath may have a proximal end which is tapered and smoothed to present a low resistance to advancement of the introducer during insertion. The proximal end of the external sheath may also be adapted to have a tight fit onto the proximal attachment device.

Preferably the distal attachment device is of a streamlined shape and is adapted to be advanced to the proximal attachment device whereby to allow smooth retrieval through the released prosthesis and into the external sheath for removal from a patient.

The introducer according to this invention may be used with a straight tubular self expanding prosthesis or it may be used where the prosthesis is a bifurcated prosthesis.

The introducer according to this invention may be used where the lumen of the patient is an aorta and the prosthesis is adapted to repair an aortic aneurism.

In an alternative form the invention is said to reside in a method of placing a prosthesis into an internal lumen by means of an insertion assembly the method including the steps of; inserting the insertion assembly including the prosthesis into the internal lumen, withdrawing a sheath from the insertion assembly to expose the prosthesis, releasing the prosthesis from the insertion assembly, replacing the sheath onto the insertion assembly, and retracting the insertion assembly.

Preferably the prosthesis has a proximal end and a distal end and the insertion assembly includes a proximal attachment device and a distal attachment device adapted to retain the proximal and distal ends of the prosthesis respectively and the step of releasing the prosthesis includes the steps of releasing the proximal end and then the distal end.

The step of replacing the sheath onto the insertion assembly may include the step of advancing the distal attachment device up to the proximal attachment device and withdrawing the two devices together.

Between steps (b) and (c) the prosthesis may be manipulated by respective movements longitudinally and rotationally of the proximal attachment device and distal attachment device to correctly position the prosthesis.

Where the prosthesis is a bifurcated prosthesis the step of withdrawing the sheath may include the steps of withdrawing the sheath to a first position in which a side arm of the prosthesis is exposed, insertion of an extension prosthesis into the side arm and then full removal of the sheath from the prosthesis.

Preferably the step of insertion of the extension prosthesis into the side arm comprises the steps of, inserting an extension insertion assembly into the side arm, the extension insertion assembly including a top guide mounted on a catheter, an extension prosthesis on the catheter and a sheath retaining the extension prosthesis and extending over the top guide, withdrawing the sheath to expose and deploy the extension prosthesis, withdrawing the sheath, top guide and catheter together.

The top guide may include a long proximal nose extension and the catheter may include a distal stop with the extension prosthesis being mounted between the distal stop and the top guide.

In an alternative form the prosthesis is a bifurcated prosthesis and the step of withdrawing the sheath includes the steps of withdrawing the sheath to a first position in which a first side arm of the prosthesis is exposed, insertion of a first extension prosthesis into the first side arm, then full removal of the sheath from the prosthesis to expose a second side arm and then insertion of a second extension prosthesis into the second side arm.

The steps of insertion of the first and second extension prosthesis into the first and second side arms comprises the same steps as discussed above.

In a further form the invention is said to reside in an intraluminal prosthesis having a tubular graft and a plurality of self expanding stents along the length of the graft, the prosthesis having a proximal end and a distal end, the prosthesis being characterised by the stents at the proximal end and at the distal end being inside the tubular graft and the remainder of the stents being on the outside of the graft.

There may be further included a further self expanding stent mounted to the proximal end of the graft and extending beyond the said proximal end. The further stent may include attachment devices. The attachment devices may comprise barbs extending towards the distal end of the prosthesis.

The prosthesis may be bifurcated at its distal end to provide a shorter prosthesis leg and a longer prosthesis leg. The shorter leg may have a terminal stent on the outside of the prosthesis and the longer leg have the internal distal stent.

There may also be an extension prosthesis for insertion into the shorter prosthesis leg, the extension prosthesis comprising a tubular extension prosthesis and a plurality of self expanding stents, the extension prosthesis having a proximal end and a distal end, stents at the proximal and distal ends being inside the tubular extension prosthesis and the remaining stents being on the outside of the prosthesis.

The intraluminal prosthesis may be constructed so that both the shorter leg and longer leg have external terminal stents and extension prostheses for each leg, each extension prosthesis comprising a tubular extension prosthesis and a plurality of self expanding stents, the extension prosthesis having a proximal end and a distal end, stents at the proximal and distal ends being inside the tubular extension prosthesis and the remaining stents being on the outside of the prosthesis.

Each stent of the intraluminal prostheses according to this invention may be a zig-zag stent.

Generally it will be seen that by this invention there is provided an arrangement by which a prosthesis can be compressed into a thin insertion device and then the insertion device advanced through a vessel such as a femoral artery until the prosthesis is substantially in the position required and then by careful positioning before release of the attachment means at a proximal end of the prosthesis and then repositioning if necessary before release of the distal end of the prosthesis, the prosthesis can be placed and released accurately.

DETAILED DESCRIPTION OF EMBODIMENTS OF THE INVENTION

The construction of preferred embodiments and the method by which the device may be operated may be made clearer with the aid of the accompanying drawings which show preferred embodiments of the invention and the method by which the device of the various embodiments may be used. For the purpose of clarity the lumens or vessels into which the prosthesis has to be inserted is not been shown in the drawings except in FIG. 18.

Figure 2:
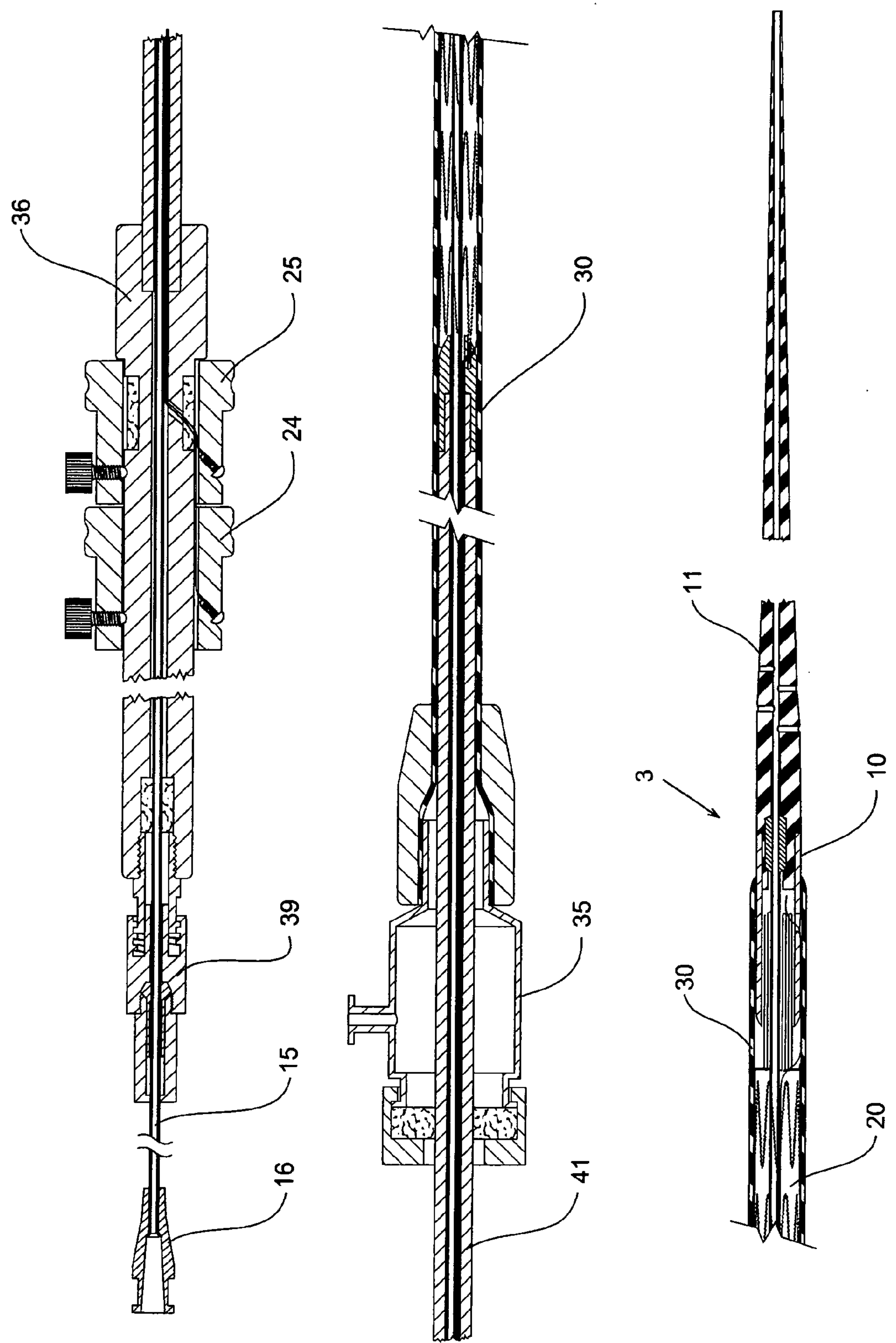
Figure 3:
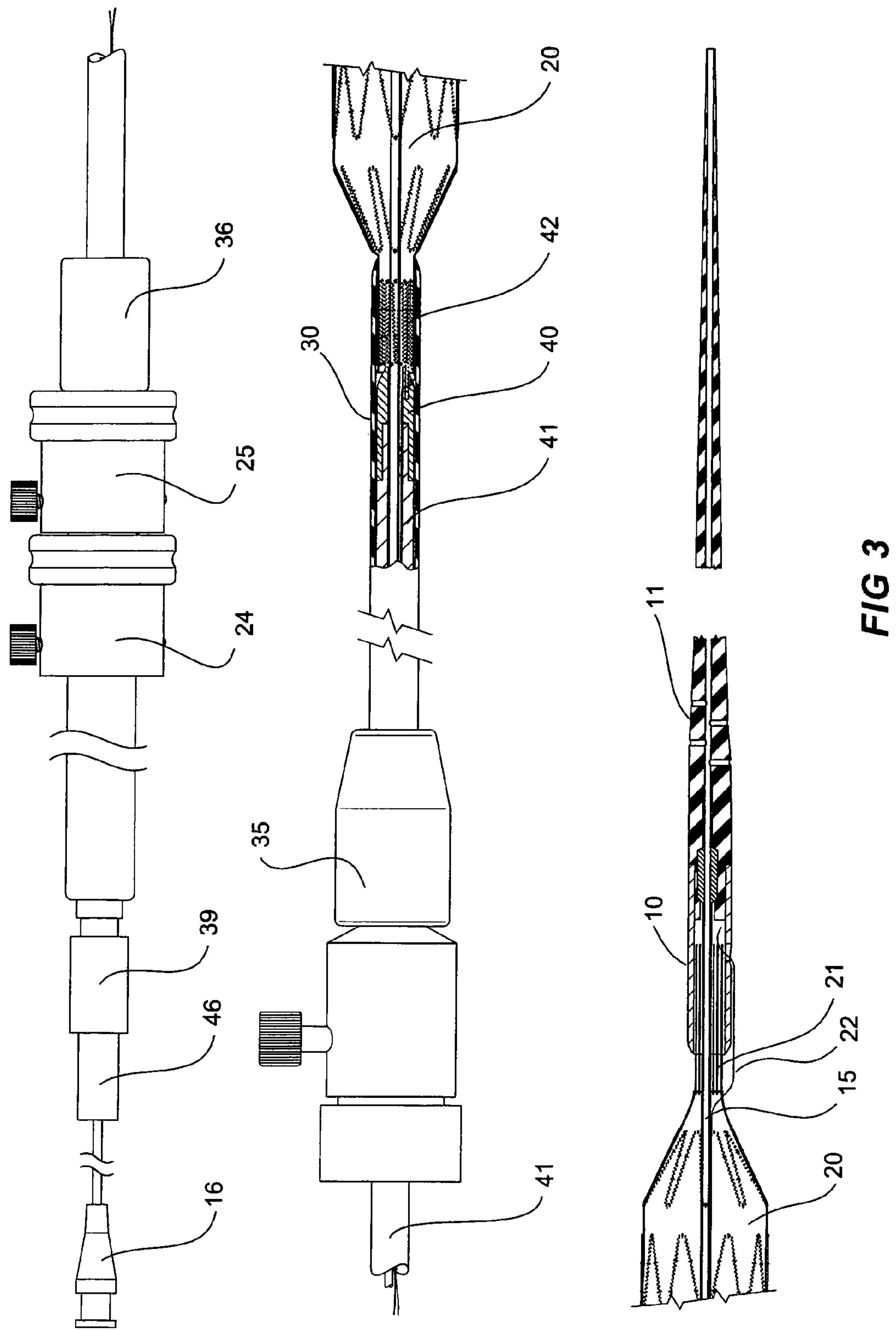
Figure 4:
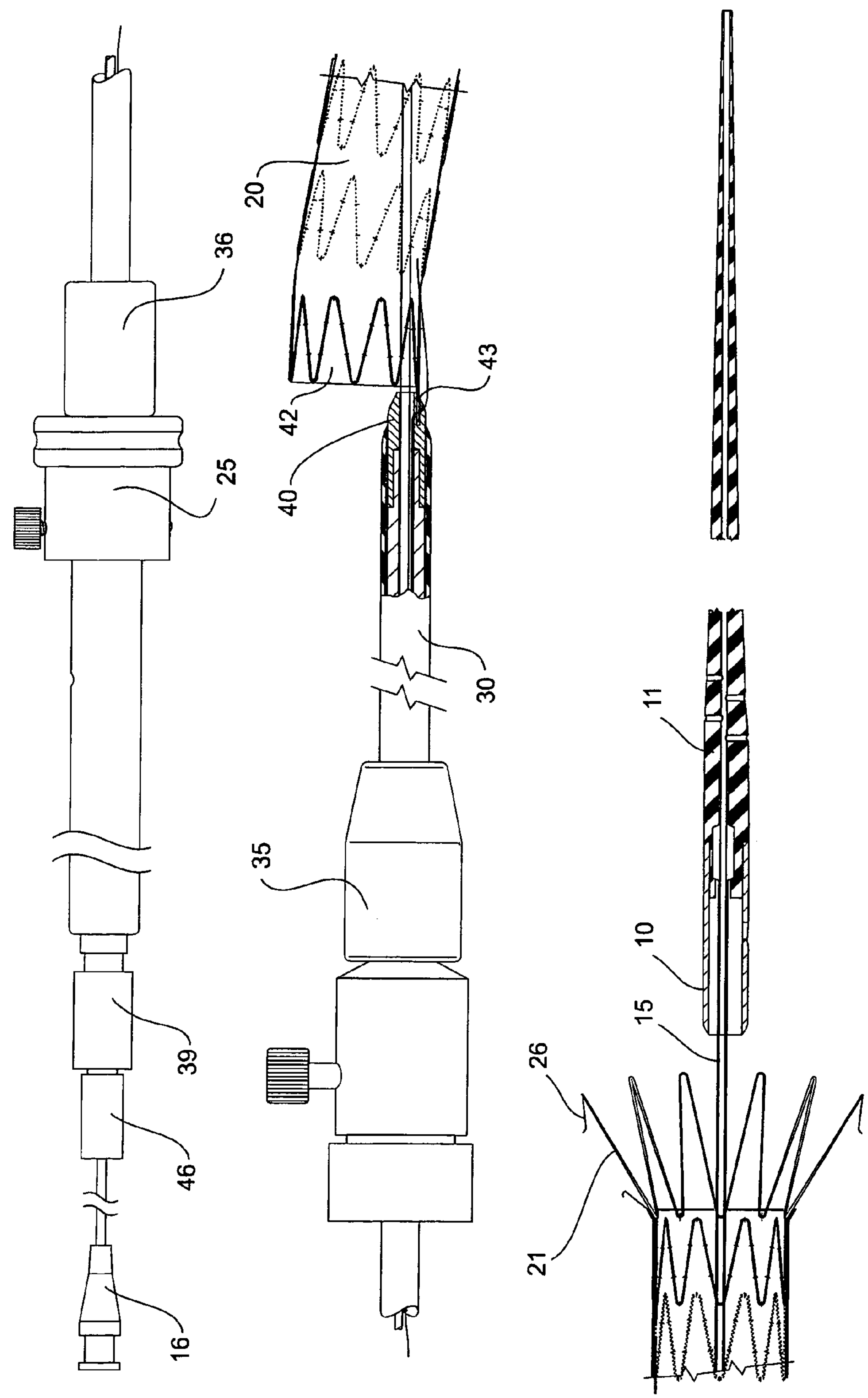
Figure 5:
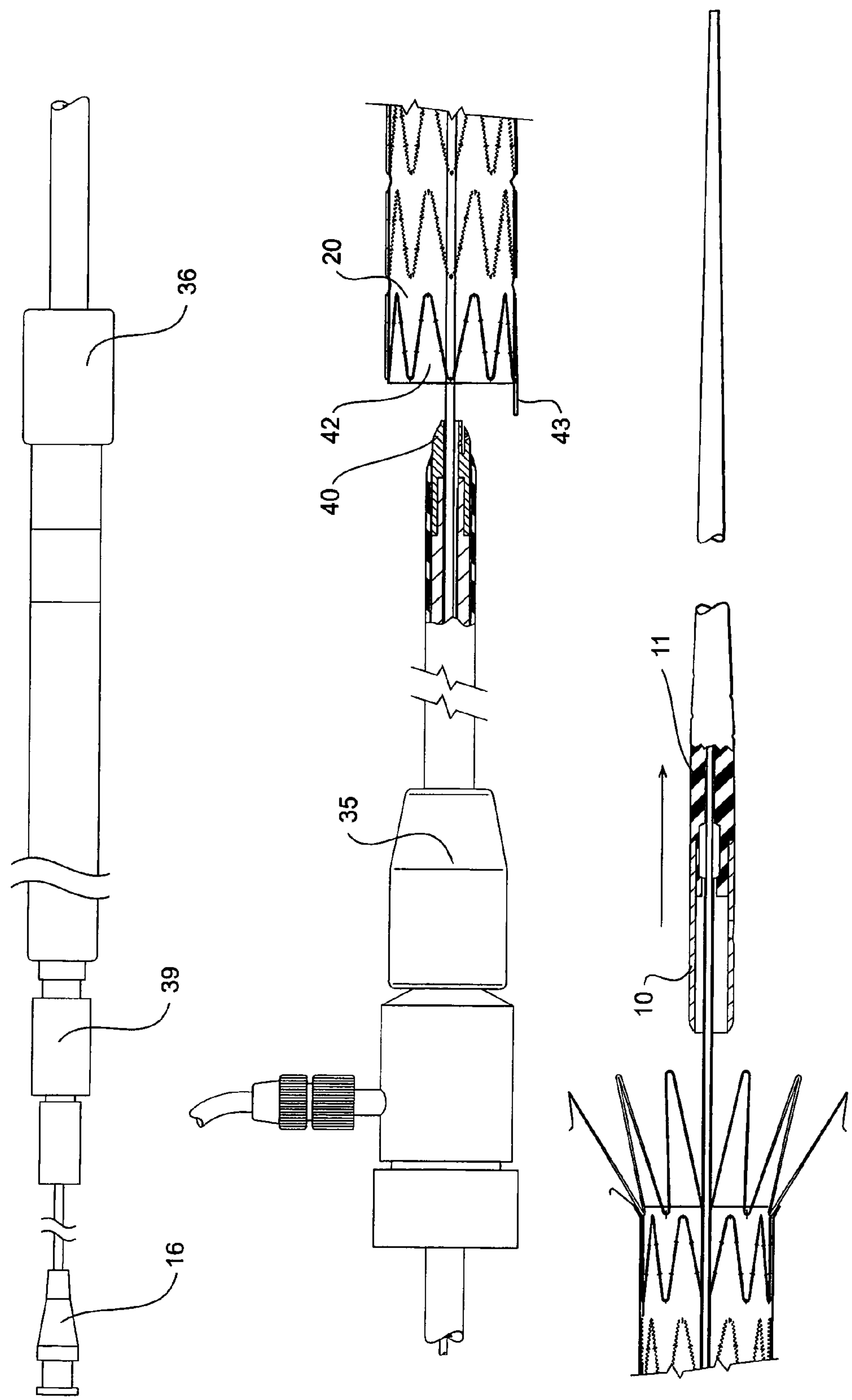
Figure 6:
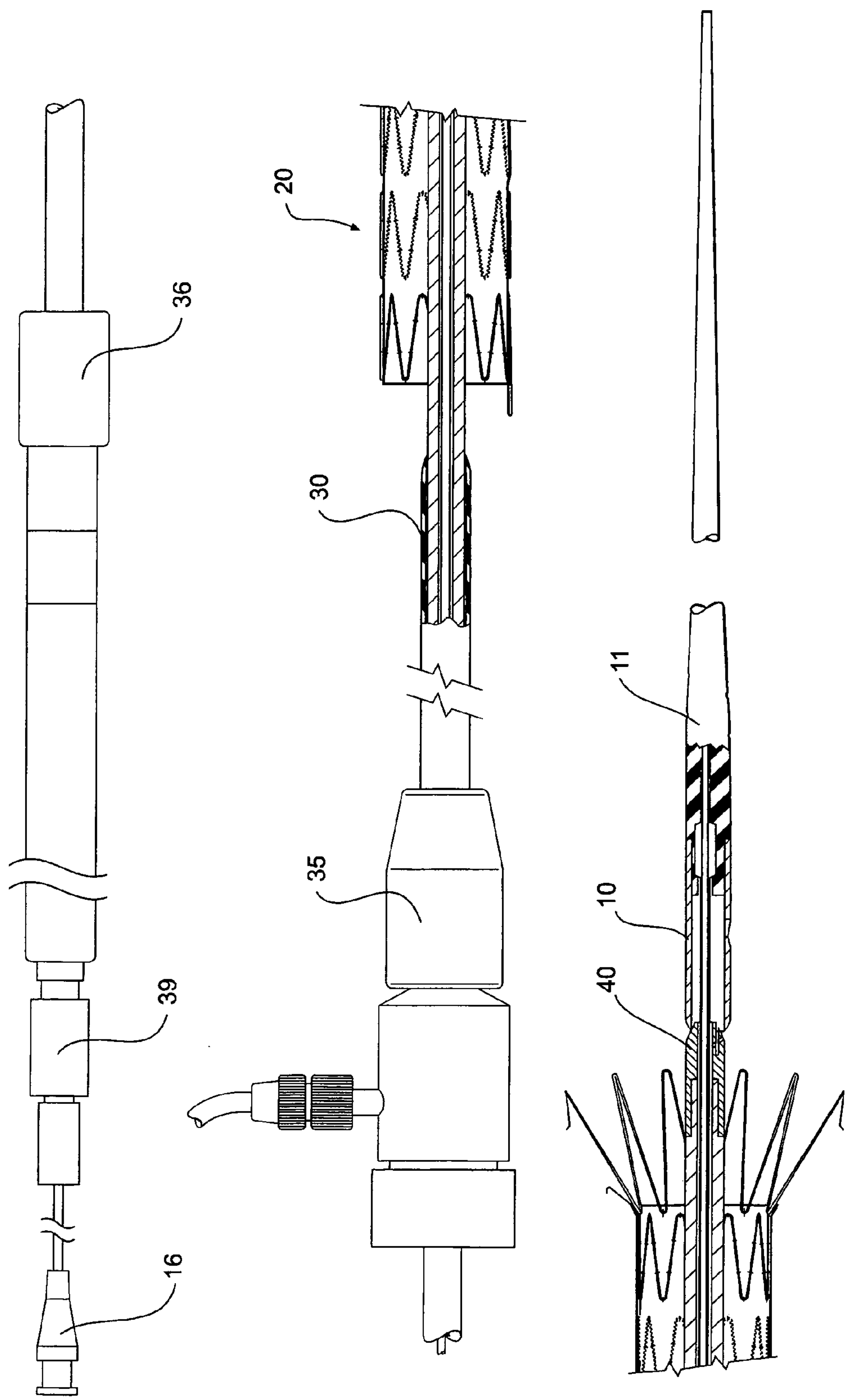
Figure 7:
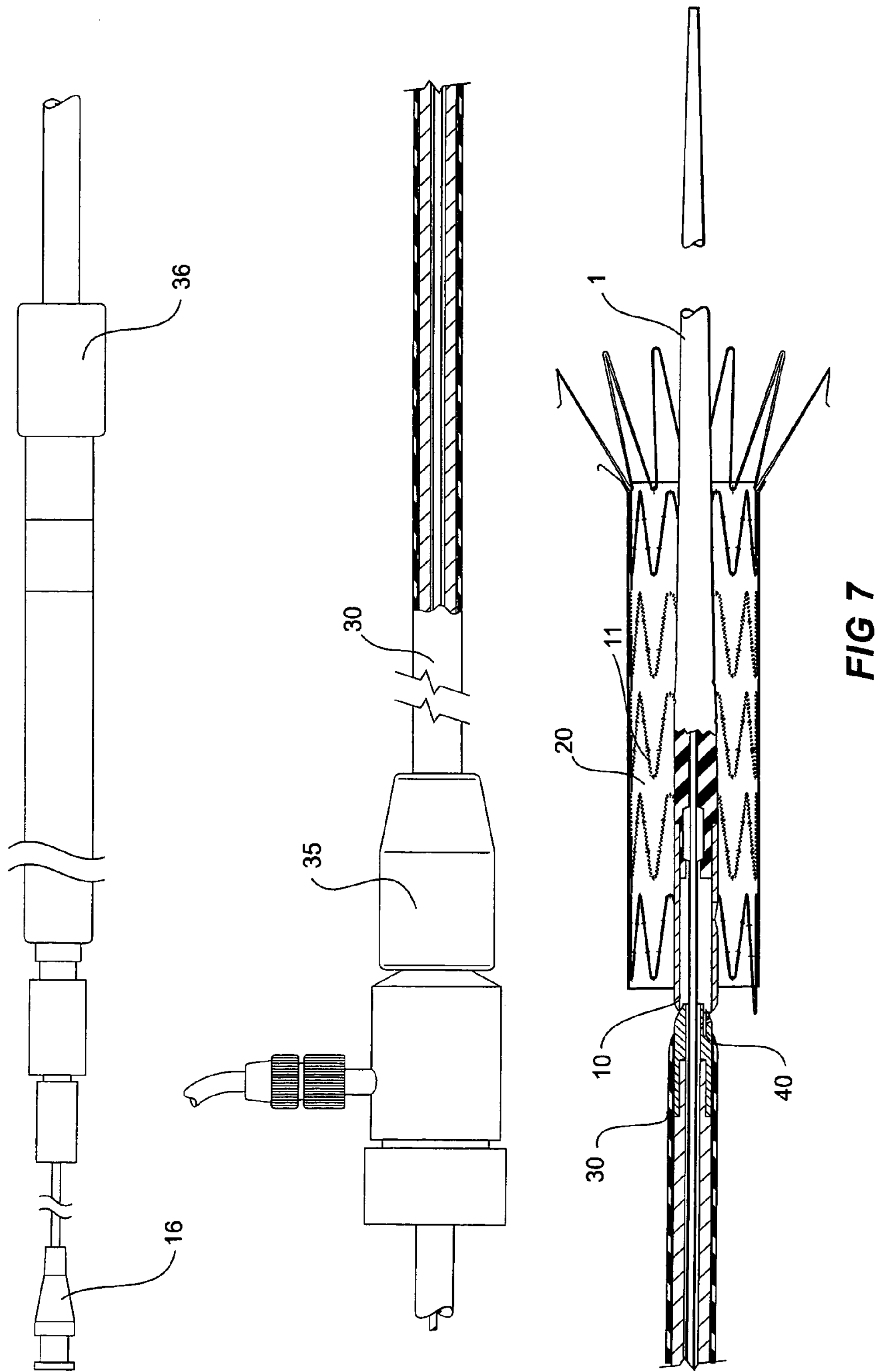
Figure 8:
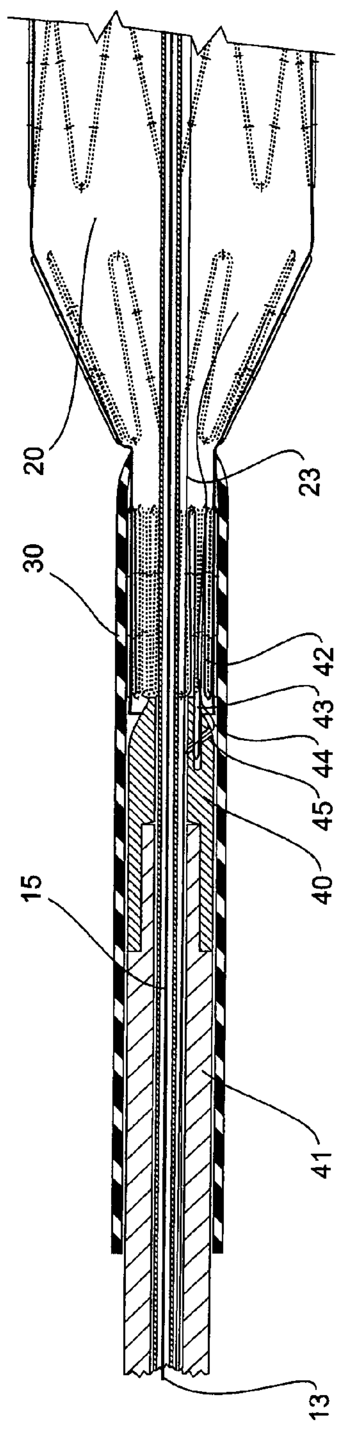
Figure 9:
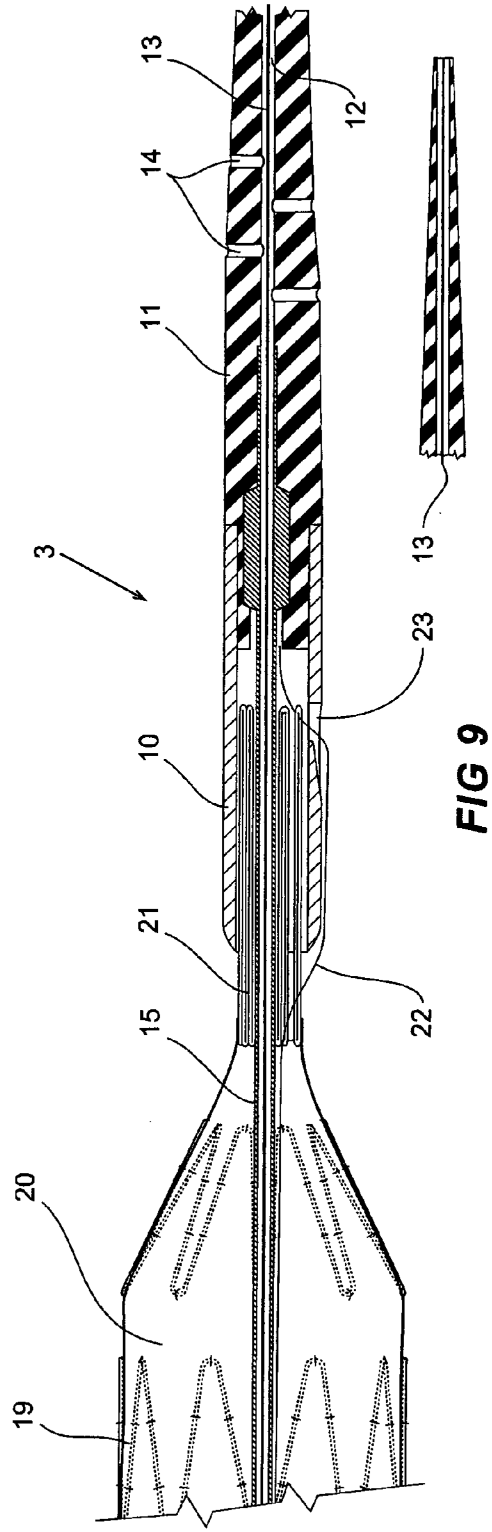
Figures 8A, 8B:
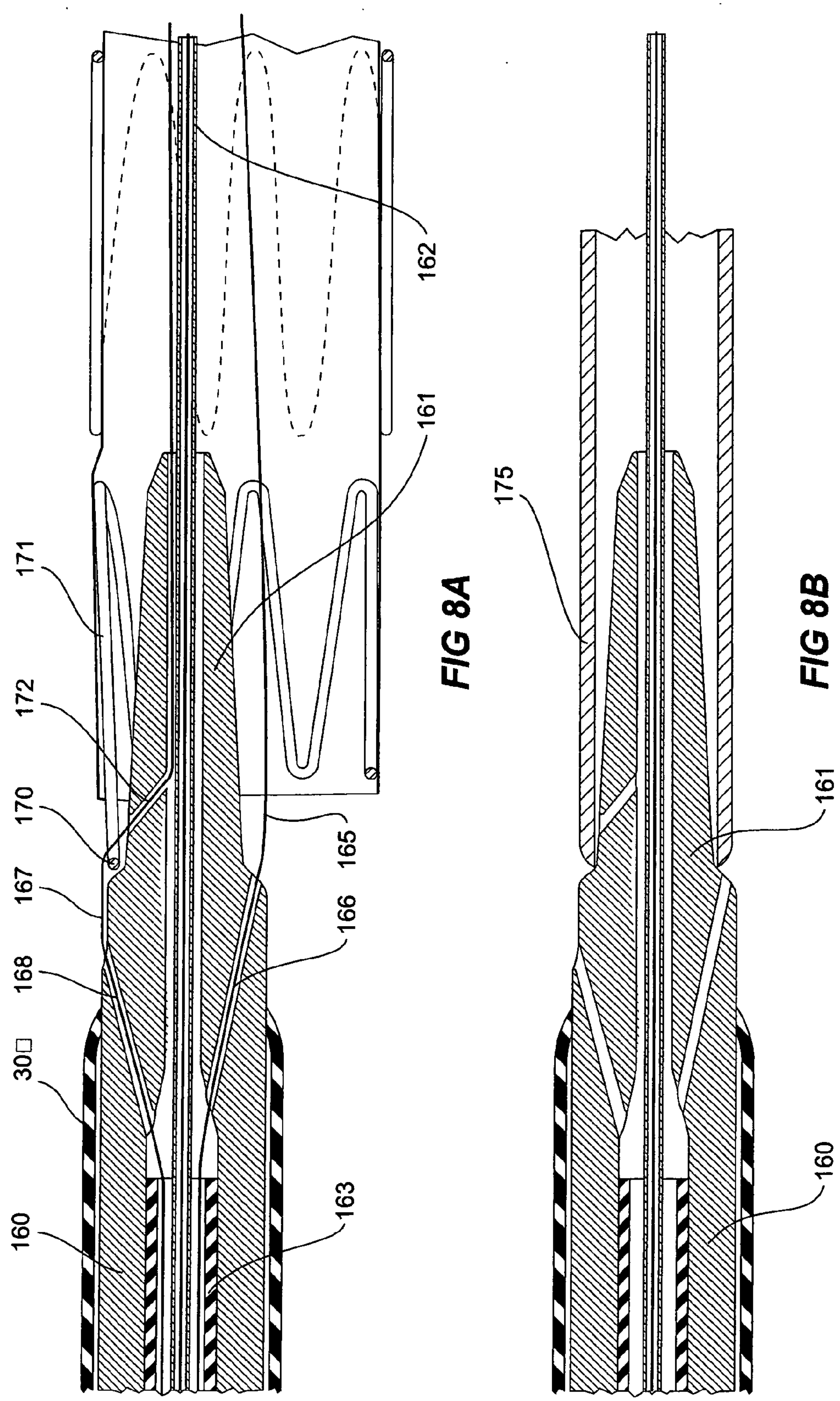
Figure 10:
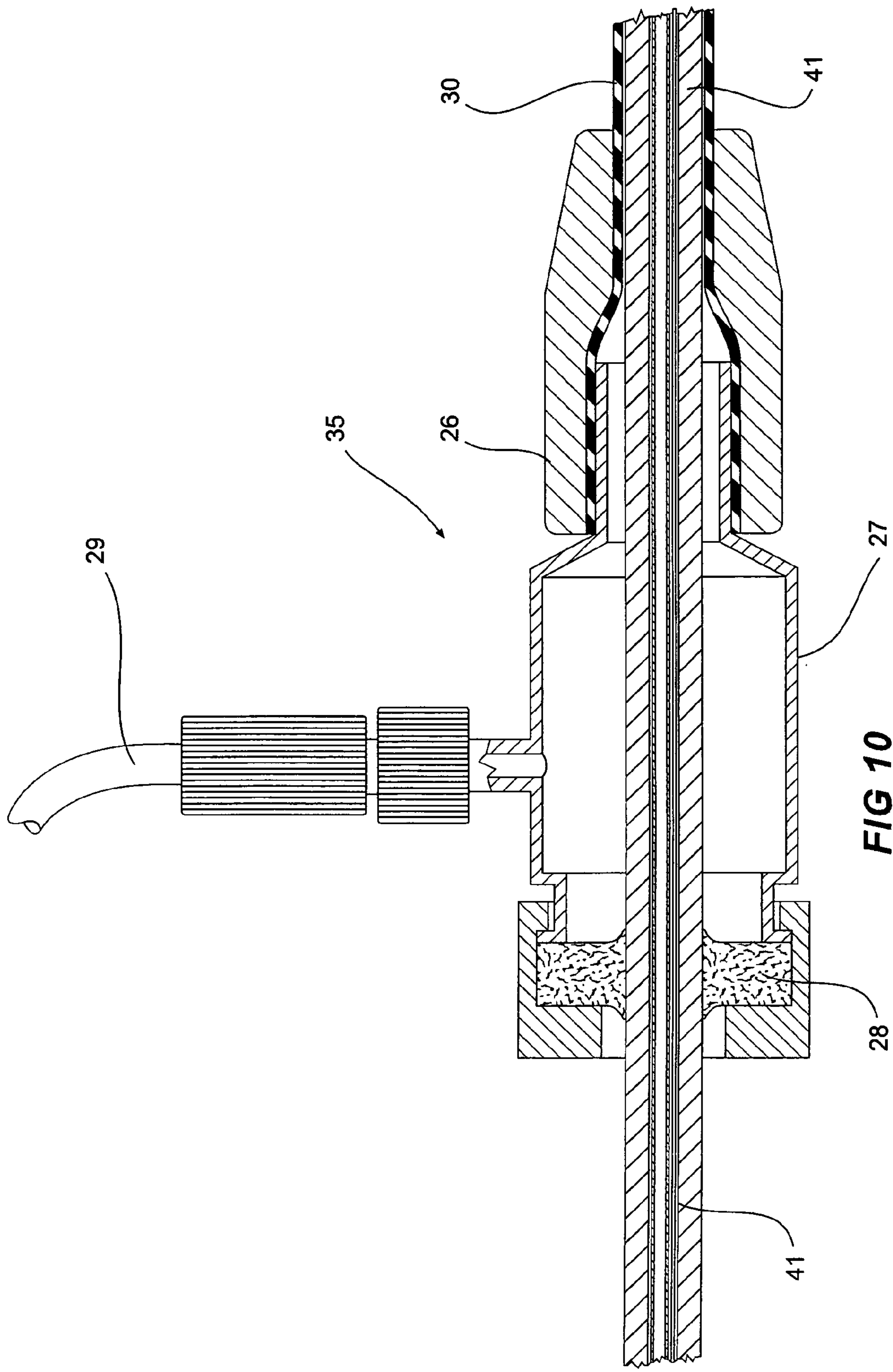
Figure 11:
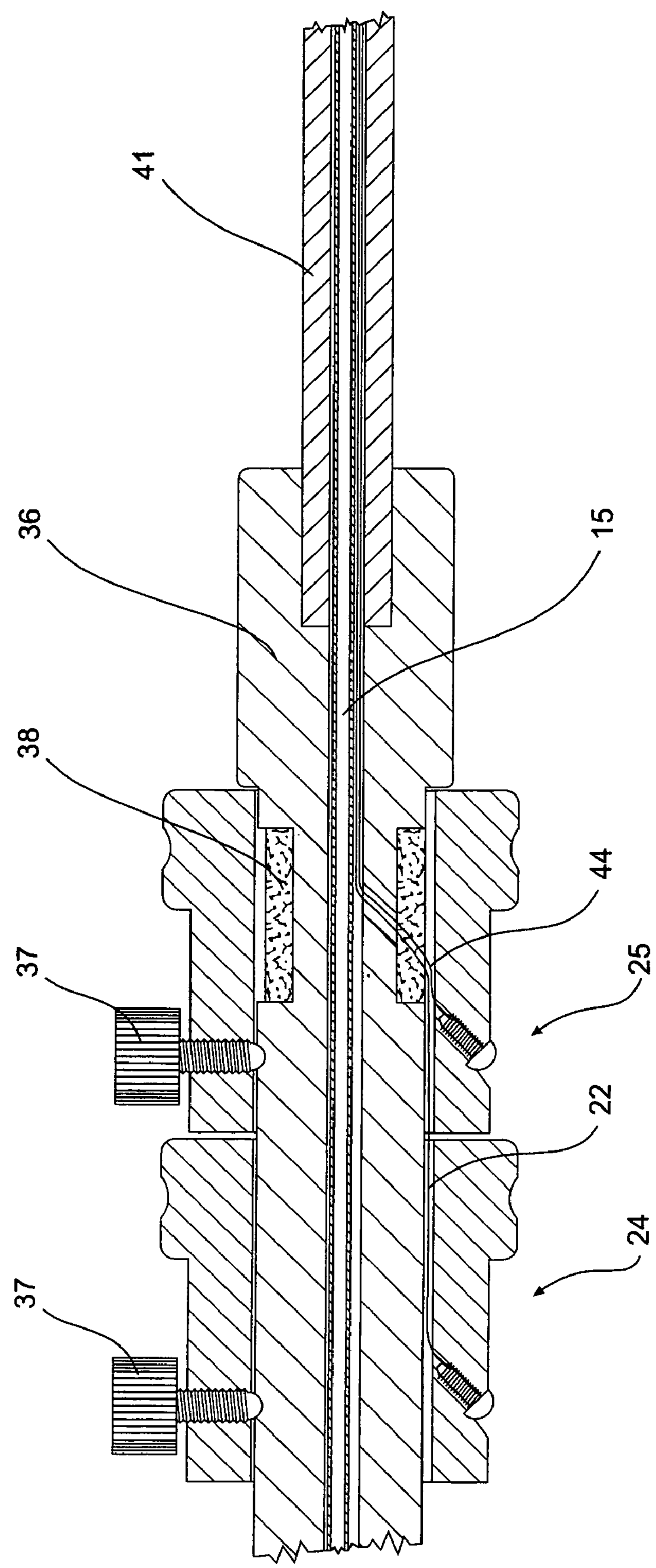
Figure 12:
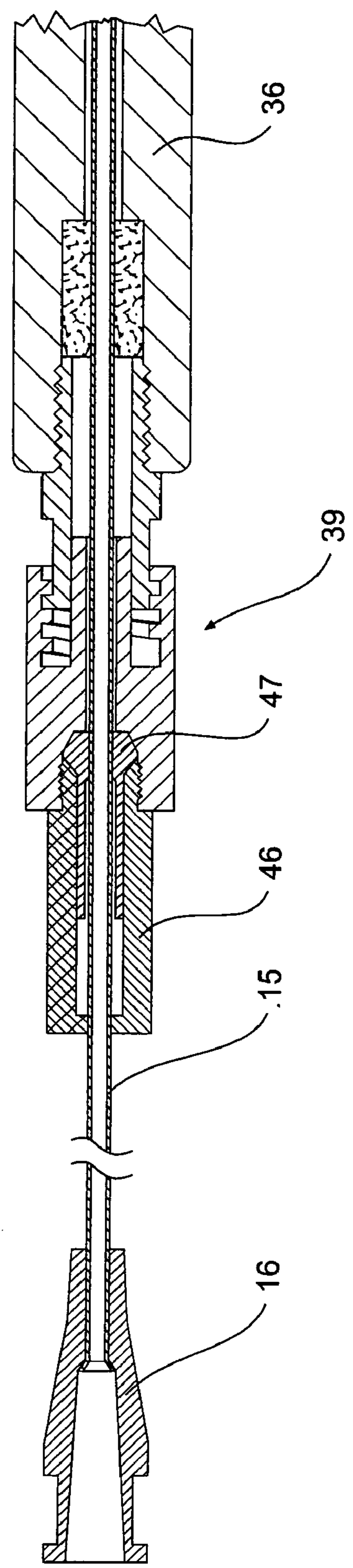
Figure 13A:
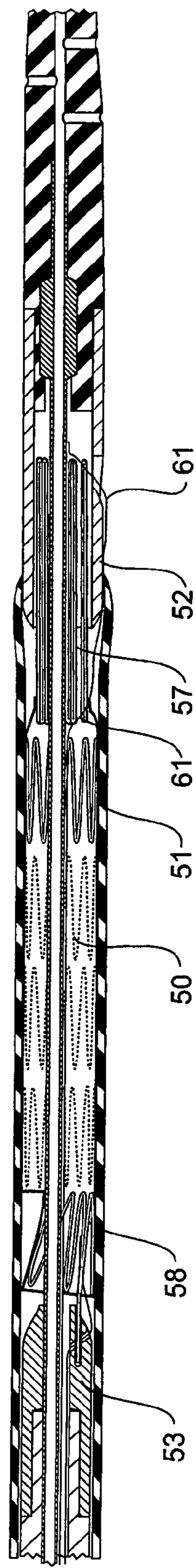
Figure 13B:
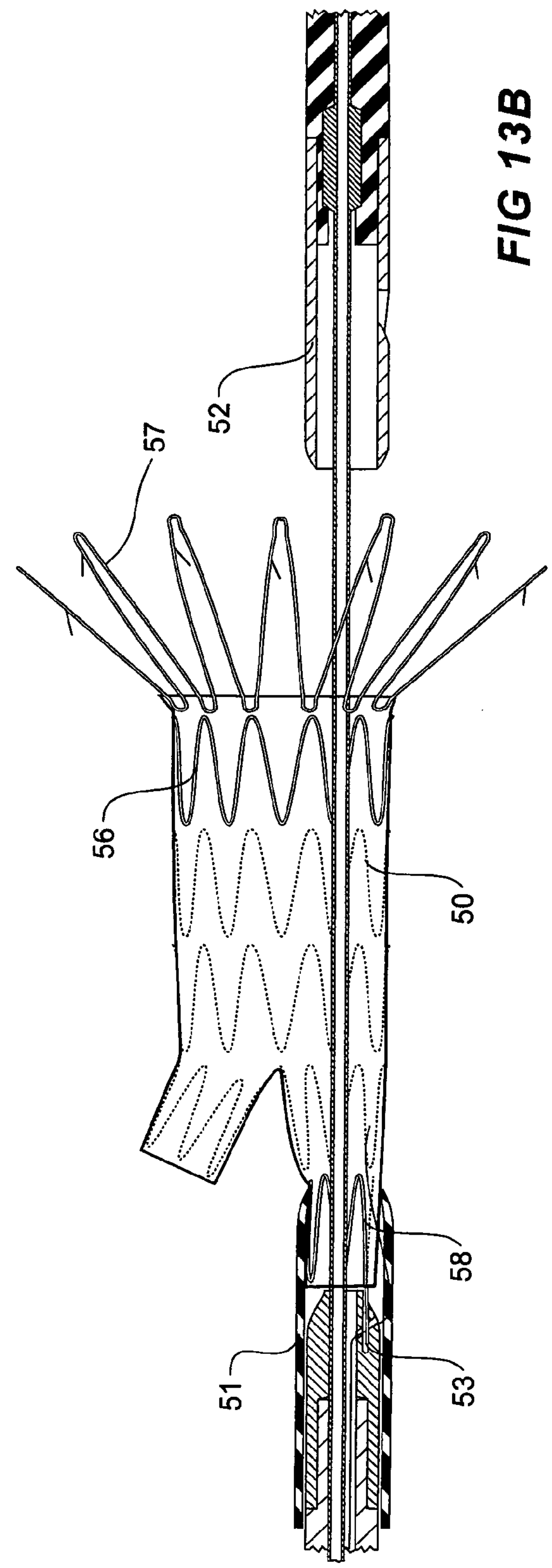
Figure 13C:
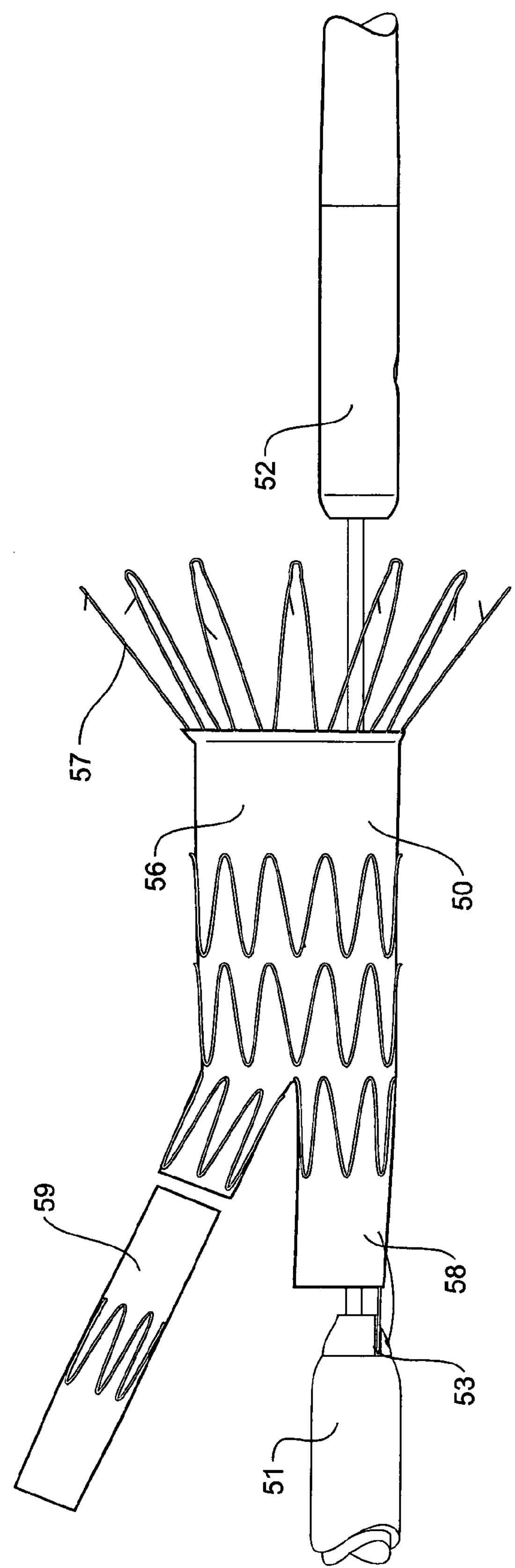
Figure 14:
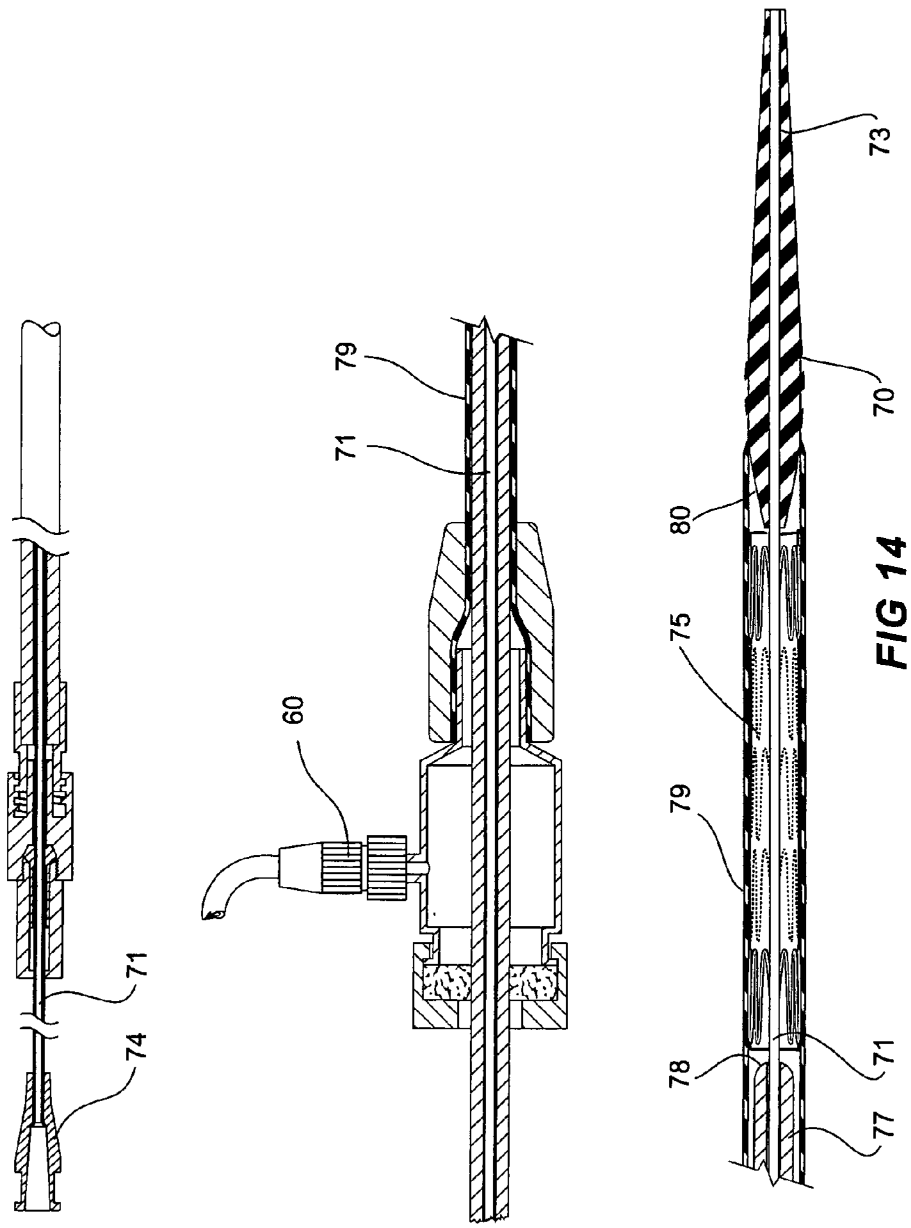
Figures 15, 16:
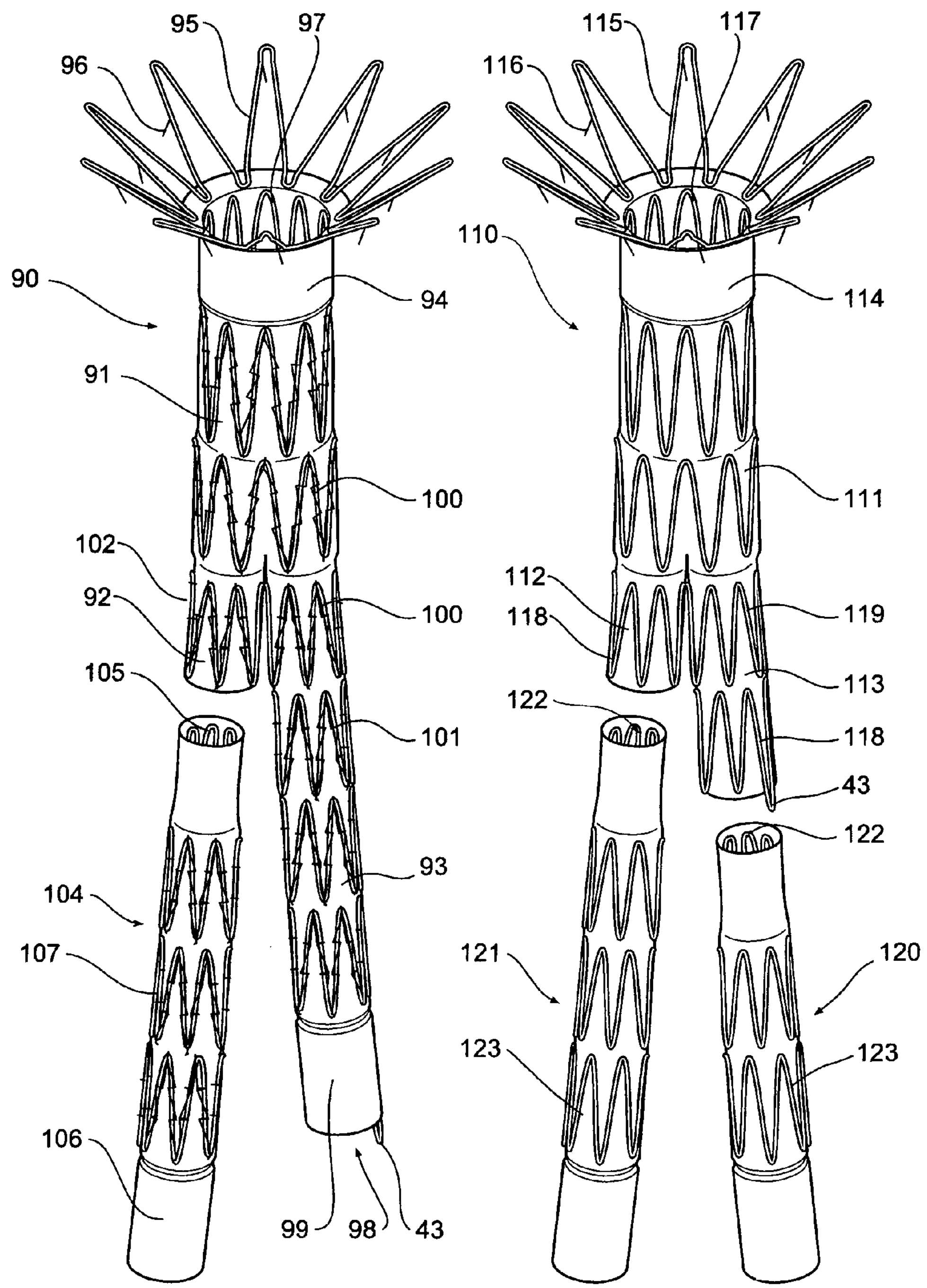
Figure 17:
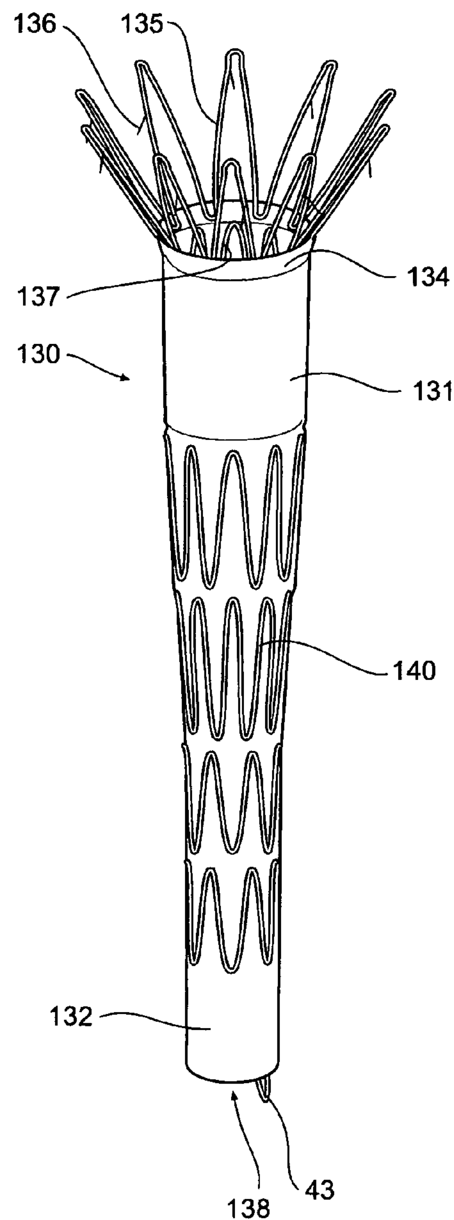
Figure 18:
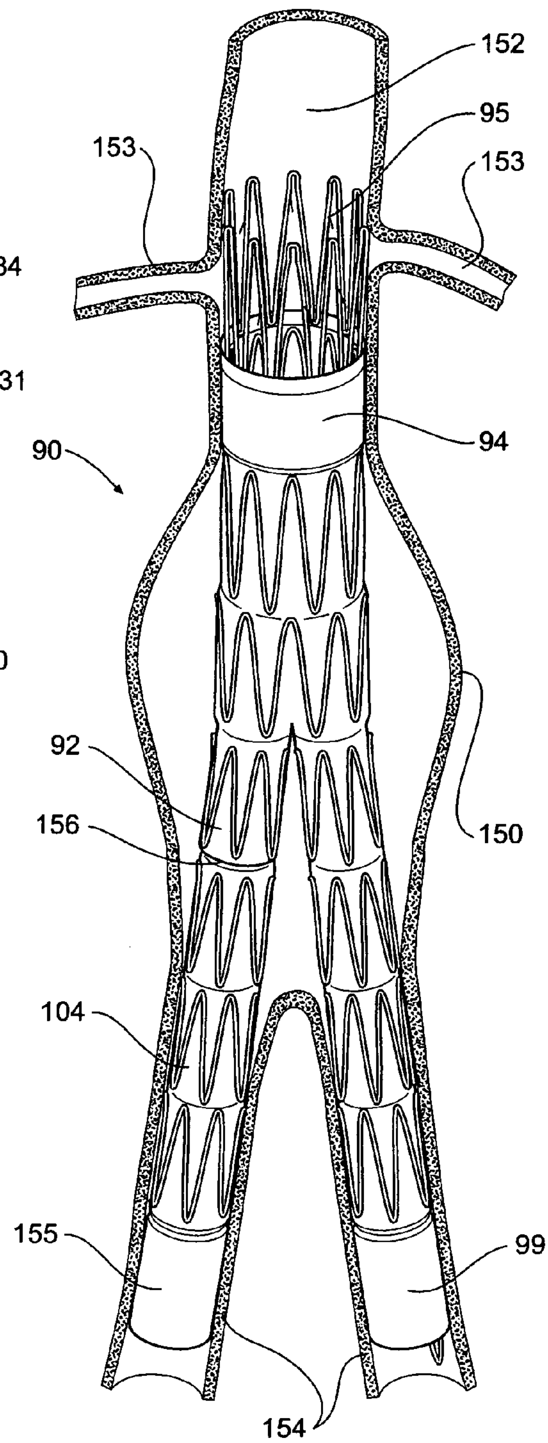

In the drawings:

FIG. 1 shows a first embodiment of an introducer according to this invention in perspective view with the prosthesis partially deployed, FIG. 2 shows the first embodiment of the introducer as shown in FIG. 1 being fully loaded and ready for introduction into a patient, FIG. 3 shows the embodiment of FIG. 2 in the next stage of deployment of the prosthesis, FIG. 4 shows the embodiment of FIG. 2 with the release of the proximal end stage of deployment, FIG. 5 shows the release of the distal end stage of deployment, FIG. 6 shows the advancement of the distal attachment device to the proximal attachment device, FIG. 7 shows the withdrawal of the introducer, FIG. 8 shows that part of the introducer around the distal end of the prosthesis in detail, FIG. 8A shows an alternative embodiment of that part of the introducer around the distal end of the prosthesis in detail, FIG. 8B shows the embodiment of FIG. 8A with the distal attachment device advanced to the proximal attachment device, FIG. 9 shows that part of the introducer around the proximal end of the prosthesis in detail, FIG. 10 shows that part of the introducer around the haemostatic seal in detail, FIG. 11 shows that part of the introducer around the trigger wire release mechanisms in detail, FIG. 12 shows that part of the introducer around the pin vise clamp and the medical reagent introduction tube in detail, FIGS. 13A-13C show portions of an alternative embodiment of introducer according to this invention adapted for introduction of a bifurcated prosthesis, FIG. 14 shows an alternative embodiment of introducer according to this invention adapted for introduction of an extension prosthesis, FIG. 15 shows an embodiment of a bifurcated prosthesis with an extension prosthesis according to this invention, FIG. 16 shows an embodiment of a bifurcated prosthesis with two extension prostheses according to this invention, FIG. 17 shows an embodiment of a prosthesis according to this invention intended for aortouni-iliac deployment, and FIG. 18 shows a deployed prosthesis according to this invention within an aorta with an aneurism.

Now looking more closely at the drawings and particularly in the embodiment shown in FIGS. 1-12 it will be seen that an endovascular arrangement such as the introducer according to this invention comprises generally an external manipulation section 1, a distal attachment region 2 and a proximal attachment region 3.

The proximal attachment region 3 shown in detail in FIG. 9 includes a cylindrical sleeve 10 with a long tapered flexible extension 11 extending from its proximal end. The extension 11 has an internal longitudinal aperture 12 to enable it to be advanced along an insertion wire 13 and to enable the supply of medical reagents such as by the use of a contrast agent to allow angiography to be performed during placement and deployment phases of the medical procedure. A thin walled metal tube 15 is fastened to the extension 11 and extends through the complete introducer to the manipulation section and terminates in a connection means 16 (FIG. 1) for a syringe so that the medical reagent may be introduced into the metal tube and subsequently into the extension 11 to emanate through the apertures 14. The thin walled metal tube 15 is flexible so that the introducer can be advanced along a relatively tortuous vessel such as the femoral artery and also to allow manipulation longitudinally and rotationally of the proximal attachment region 3.

The prosthesis 20 is of a self expanding type having resilient stents 19 to enable it to expand after it is released from the introducer. The prosthesis retained within the introducer includes a self expanding zigzag stent 21 extending from its proximal end; and in the compressed condition the zigzag stent 21 is retained in the cylindrical sleeve 10 of the proximal attachment region 3, and is retained therein by means of a trigger wire 22 which extends through an aperture 23 in the side of the proximal attachment device 10 and is received in one of the loops of the zigzag stent. The trigger wire 22 extends along most of the length of the introducer and exits at the manipulation region at a proximal wire release mechanism 24 (FIGS. 1 and 11).

The prosthesis 20 is retained in its compressed condition by means of an external sleeve 30 which is advanced to be received over the cylindrical sleeve 10 of the proximal attachment device 10 when the device is assembled for insertion as can be particularly seen in FIG. 2. The external sheath 30 extends distally to external of a patient to the external manipulation section and a gripping and haemostatic sealing means 35 thereof.

As can be particularly seen in FIG. 8, the distal end of the prosthesis 20 is retained in the distal attachment device 40 which is mounted onto a thick walled plastics tube 41 which extends distally to external of the patient and to the manipulation region 1. The thick walled tube is coaxial with and radially outside the thin walled tube 15 and the sheath 30 is coaxial with and radially outside the thick walled tube 41. The distal end 42 of the prosthesis 20 has a loop 43 through which a distal trigger wire 44 extends. The distal trigger wire extends through an aperture 45 on the distal attachment device into the annular region between the thin walled tube 15 and the thick walled tube 41 like the proximal trigger wire which also extends through the annular space between the thick walled tubing 41 and the thin walled tubing 15 to the manipulation device and out at a distal wire release mechanism 25 as depicted in FIGS. 2 and 11.

In the alternative embodiment as shown in FIGS. 8A and 8B, the thick walled tube 160 has a tapered end 161 through the thin walled tube 162 extends. A low friction lining 163 is provided between the thick walled tube 160 and the thin walled tube 162 so that the former slides easily over the latter. The proximal release wire 165 and the distal release wire 167 are within the thick walled tube 160 and extend out respective apertures 166 and 168 distal of the tapered portion 161. The distal release wire 167 passes through the loop 170 in the distal end of the prosthesis 171 and re-enters the tapered portion 161 through aperture 172.

As shown in FIG. 8B when the distal attachment region has been advanced to the proximal attachment region the tapered portion 161 fits into the tube 175 to provide a smooth surface for the retraction of the two together.

As can be particularly seen in FIG. 10 the haemostatic sealing means 35 which remains external of a patient in use has a clamping collar 26 which clamps the external sleeve 30 to the haemostatic seal 27. The haemostatic seal 27 has a silicone seal ring 28 to seal against the thick walled tubing 41 to provide the haemostatic seal and a side tube 29 for the introduction of medical reagents between the thick walled tubing 41 and the external sleeve 30.

As can be particularly seen in FIG. 11 the release wire actuation section of the external manipulation section has a body 36 into the end of which is mounted the thick walled tubing 41 and through which passes the thin walled tube 15. Both the proximal wire release mechanism 24 and the distal wire release mechanism 25 are mounted for slidable movement on the body 36. Their positioning is such that the proximal wire release mechanism 24 must be moved before the distal wire release mechanism 25 can be moved. This means that the distal end of the prosthesis cannot be released until the proximal end of the prosthesis has been released. Clamping screws 37 are provided on each of the proximal wire release mechanism 24 and distal wire release mechanism 25 to prevent inadvertent early release of either end of the prosthesis. A haemostatic seal 38 is provided so the respective release wires can extend out through the body 36 to the respective release mechanisms.

As can be particularly seen in FIG. 12 there is a pin vise 39 mounted onto the other end of the body 36 from the thick walled tube 41. The pin vise 39 has a screw cap 46 which when screwed in, clamps vise jaws 47 against the thin walled metal tube 15 so that the thin walled tube 15 can only move with the body 26 and hence the thin walled tube can only move with the thick walled tube 41. With the clamp tightened the entire assembly except the external sleeve 30 can be moved as one.

We now look at FIGS. 2 to 7 which show the various stages of the deployment of the prosthesis according to this embodiment of the invention.

A guide wire (not shown) is introduced into the femoral artery and advanced until its tip is above the region into which the prosthesis is to be deployed.

In FIG. 2 the introducer assembly is shown fully assembled ready for introduction into a patient. The prosthesis 20 is retained at each of its ends by the proximal and distal retaining assemblies respectively and compressed by the external sleeve 30. If it is an aortic aneurism which is to be grafted the introducer assembly can be inserted through a femoral artery over the guide wire in the form as shown in FIG. 2 and positioned by radiographic techniques (not discussed here).

In FIG. 3 it will be seen that once the introducer assembly is in a selected position the external sheath 30 is withdrawn to just proximal of the distal attachment device 40 so that the prosthesis 20 is now released so that it can expand radially except where the most proximal zigzag stent 21 is still retained within the proximal attachment device 10 and where its distal end 42 is retained within the external sheath 30.

By release of the pin vise 39 to allow small movements of the thin walled tubing 15 with respect to the thick walled tubing 41, the prosthesis 20 may now be lengthened or shortened or rotated or compressed to accurately position the prosthesis in the desired place within the body lumen. X-ray opaque markers (not shown) may be placed at known locations along the prosthesis to assist with placement of the prosthesis.

In FIG. 4 the proximal trigger wire 22 (FIG. 3) has been withdrawn by distal movement of the proximal wire release mechanism 24 (FIG. 3). At this stage the proximal wire release mechanism 24 and the proximal trigger wire 22 have been removed completely by passing the proximal wire release mechanism 24 over the pin vise 39 and the connection means 16 for a syringe. The screw cap 46 of the pin vise 39 is then loosened so that the thin walled tubing 15 can been pushed in a proximal direction to move the proximal attachment means 10 in a proximal direction thereby releasing the zigzag stent 21 at the proximal end of the prosthesis from the proximal attachment means 10. At this stage the hooks or barbs 26 on the zigzag stent 21 grip into the walls of the lumen to hold the prosthesis therein. From this stage the proximal end of the prosthesis cannot be moved again.

The distal end 42 of the prosthesis 42 is still retained by the distal attachment means 40 with the loop 43 retained therein. The external sheath 30 has been withdrawn to distal of the distal attachment device 40 to allow the distal end of the attachment device to expand.

At this stage, however, the distal end of the prosthesis can still be moved so that the prosthesis can be rotated or lengthened or shortened or otherwise moved to accurately position the prosthesis. Where the prosthesis to be deployed is a bifurcated graft, the movement at this stage can ensure that the shorter leg is directed in the direction of the contra-iliac artery.

In FIG. 5 the distal end 42 of the prosthesis has been released by removal of the distal trigger wire 44. At this stage the distal wire release mechanism 25 and the distal trigger wire 44 can be removed completely by passing the distal wire release mechanism 25 over the pin vise and the connection means 16 for a syringe. The loop 43 of the terminal distal zigzag stent is hence freed and the prosthesis is now free to expand to the walls of the vessel and the introducer is ready to be removed.

The first stage of removal is shown in FIG. 6 where the distal attachment device 40 is advanced to be received in the rear of the proximal attachment device 10, and then the proximal attachment device 10 including the tapered flexible extension 11 and the distal attachment device 40 are removed together as shown in FIG. 7. In this drawing the external sleeve 30 has been advanced to cover the joint between the proximal attachment device 10 and the distal attachment device 40 and is also removed with the proximal attachment device 10, the tapered flexible extension 11 and the distal attachment device 40, although these could be removed separately and then the external sleeve 30 removed later. This may have some advantage if further surgical procedures are necessary, as a clear way is provided to advance other surgical equipment.

FIG. 13A to FIG. 13C shows the use of the introducer according to this invention with a self expanding bifurcated prosthesis.

In FIG. 13A to FIG. 13C is shown the section of the introducer including the proximal attachment device and the distal attachment device of the introducer with a bifurcated prosthesis.

The bifurcated prosthesis 50 is retained within the external sheath 51 between the proximal attachment device 52 and the distal attachment device 53 with respective fixings to the proximal attachment device 52 and the distal attachment device 53 being the same as shown in FIGS. 1 to 12. The proximally extending zigzag stent 57 is retained within the proximal attachment device 52.

As shown in FIG. 13B after the proximal trigger wire 61 has been released and the proximal attachment device 52 advanced, the proximal end 56 of the prosthesis 50 is released and the zigzag stent 57 is free to expand. At this stage the distal end 58 of the prosthesis 50 is still retained in the distal attachment means 53.

At this stage an extension piece 59 can be inserted into the side arm 60 by a separate introducer (see FIG. 14) from the other femoral artery for securing to the short leg of prosthesis 50 as shown in FIG. 13C. The release of the distal attachment device and the withdrawal of the introducer can the proceed in the same manner as discussed with respect to FIGS. 1 to 12.

An embodiment of introducer according to this invention suitable for the introduction of an extension prosthesis is shown in FIG. 14 which shows the various portions of the introducer along its length.

Commencing from the proximal end the embodiment includes a tapered flexible extension 70 mounted on a thin walled metal tube 71. The tapered flexible extension 70 includes a longitudinal aperture 73. The thin walled metal tube 71 is fastened to the tapered flexible extension and extends in a distal direction from the tapered flexible extension to external of the patient, in use. The thin walled metal tube 71 extends to a connector 74 for the introduction of medical reagents as necessary. There are no proximal or distal attachment devices on the extension prosthesis introducer. The prosthesis 75 is retained between the distal end 80 of the flexible extension and the proximal end 78 of a thick walled flexible tube 77. A sheath 79 is in a sliding fit on the thick walled tube 77 and during the insertion process is fitted over the extension prosthesis up to the distal end 80 of the flexible extension 70 to provide a smooth surface for the progression of the introducer through the vascalature.

The method of introduction of the extension prosthesis is as follows.

A guide wire (not shown) is introduced into the femoral artery and advanced until its tip is above the region into which the prosthesis is to be deployed. The introducer is then advanced over the guide wire with an oscillating rotating action until the extension prosthesis is overlapped one full stent within the shorter leg of the prosthesis. A final position check may than be made before the sheath 79 is withdrawn while holding the thick walled tube 77 in place. The introducer can then be removed by withdrawing the flexible extension 70 to the thick walled tube 77 and covering the gap between them with the sheath 79.

FIG. 15 shows an embodiment of a bifurcated prosthesis with an extension prosthesis according to this invention. The bifurcated prosthesis 90 has a generally inverted Y-shaped configuration having a body portion 91, a shorter leg 92 and a longer leg 93. The body of the prosthesis is constructed from a tubular woven synthetic material such as Dacron. At the proximal end 94 of the prosthesis 90 is a first zigzag stent 95 which extends beyond the end of the prosthesis and has distally extending barbs 96. The prosthesis has a number of zigzag stents mounted to it and extending along its length. The stent 97 nearest the proximal end 94 is inside the tubular material so that the outside presents a smooth surface which in use engages against the inner wall of the vessel into which it is deployed to provide a barrier to the flow of blood. The stent 98 nearest the distal end 99 of the longer leg is also inside the tubular material so that the outside presents a smooth surface which in use engages against the inner wall of the vessel into which it is deployed to provide a barrier to the flow of blood. Between these internal stents the rest of the stents 100 are arranged on the outside of the tubular material so that they present minimal restriction to the flow of blood through the prosthesis and present minimal sites for the growth of thromboses within the prosthesis. Each stent is sewn to the tubular material as shown particularly at 101.

The longer leg 93 has one loop 43 of the terminal internal stent 98 extending beyond the end of the tubular material to act as the distal attachment means.

In use the prosthesis according to this embodiment of the invention is adapted for fitting into an aorta such that the end 94 is just distal of the renal arteries and the first zigzag stent 95 extends up to or over the renal arteries. As it is constructed from thin wire it does not obstruct the renal arteries if it extends over them. The longer leg 93 extends down one of the iliac arteries and the shorter leg terminates in the aorta just short of the other iliac artery.

The terminal stent 102 nearest the distal end of the shorter leg 92 is outside the tubular material so that the inside presents a smooth surface which in use engages against the outside of one end of an extension prosthesis.

An extension prosthesis 104 is adapted for fitting into the shorter leg by the method as discussed above. The extension prosthesis 104 is constructed from a tubular synthetic material such as Dacron and has terminal internal stents 105 and a plurality of external intermediate stents 106.

FIG. 16 shows an embodiment of a bifurcated prosthesis with two extension prostheses according to this invention. The bifurcated prosthesis 110 has a generally inverted Y-shaped configuration having a body portion 111, a shorter leg 112 and a longer leg 113. The body of the prosthesis is constructed from a tubular woven synthetic material such as Dacron. At the proximal end 114 of the prosthesis 110 is a first zigzag stent 115 which extends beyond the end of the prosthesis and has distally extending barbs 116. The prosthesis has a number of zigzag stents mounted to it and extending along its length. The stent 117 nearest the proximal end 114 is inside the tubular material so that the outside presents a smooth surface which in use engages against the inner wall of the vessel into which it is deployed to provide a barrier to the flow of blood. The terminal stents 118 nearest the distal ends of both the shorter and longer legs are outside the tubular material so that the inside presents a smooth surface which in use engages against the outside of one end of an extension prosthesis. Between these terminal stents the rest of the stents 119 are arranged on the outside of the tubular material so that they present minimal restriction to the flow of blood through the prosthesis and present minimal sites for the growth of thromboses within the prosthesis.

The longer leg 113 has one loop 43 of the terminal external stent 118 extending beyond the end of the tubular material to act as the distal attachment means.

Extension prostheses 120 and 121 are adapted for fitting into both the shorter and longer legs by the method as discussed above. Each of the extension prostheses 120 and 121 are constructed from a tubular synthetic material such as Dacron and have terminal internal stents 122 and a plurality of external intermediate stents 123.

In use the prosthesis according to this embodiment of the invention is adapted for fitting into an aorta such that the end 114 is just distal of the renal arteries and the first zigzag stent 115 extends up to or over the renal arteries. As it is constructed from thin wire it does not obstruct the renal arteries if it extends over them. The longer leg 113 extends down one of the iliac arteries and the shorter leg terminates in the aorta just short of the other iliac artery. The extension prostheses when deployed extend down each iliac artery.

FIG. 17 shows an embodiment of a prosthesis according to this invention intended for aortouni-iliac deployment. The prosthesis 130 has a generally tapering tubular configuration having a body portion 131 extending down to a single leg 132 of lesser diameter than the body portion. The body of the prosthesis is constructed from a tubular woven synthetic material such as Dacron. At the proximal end 134 of the prosthesis 130 is a first zigzag stent 135 which extends beyond the end of the prosthesis and has distally extending barbs 136. The prosthesis has a number of zigzag stents mounted to it and extending along its length. The stent 137 nearest the proximal end 134 is inside the tubular material so that the outside presents a smooth surface which in use engages against the inner wall of the vessel into which it is deployed to provide a barrier to the flow of blood. The stent 138 nearest the distal end 132 of the leg is also inside the tubular material so that the outside presents a smooth surface which in use engages against the inner wall of the vessel into which it is deployed to provide a barrier to the flow of blood. Between these internal stents the rest of the stents 140 are arranged on the outside of the tubular material so that they present minimal restriction to the flow of blood through the prosthesis and present minimal sites for the growth of thromboses within the prosthesis.

The leg 132 has one loop 43 of the terminal internal stent 138 extending beyond the end of the tubular material to act as the distal attachment means.

In use the prosthesis according to this embodiment of the invention is adapted for fitting into an aorta such that the end 134 is just distal of the renal arteries and the first zigzag stent 135 extends up to or over the renal arteries. As it is constructed from thin wire it does not obstruct the renal arteries if it extends over them. The leg 132 extends down one of the iliac arteries. The other iliac artery is intended to be closed off with a plug (not shown) inserted via the femoral artery and a cross graft is surgically inserted between the iliac arteries to provide blood flow to both iliac arteries.

FIG. 18 shows a deployed prosthesis according to the embodiment this invention within an aorta with an aneurism.

The aneurism 150 is a ballooning of the aorta 152 between the renal arteries 153 and the iliac arteries 154. The prosthesis as shown in FIG. 15 is deployed into the aorta so that it spans the aneurism allows blood flow from the aorta to the two iliac arteries. It will be noted that the proximal portion 94 of the prosthesis 90 which has the stent on the inside bears against the wall of the aorta 152 above the aneurism so that a good seal is obtained. The zigzag stent 95 which extends beyond the portion 94 extends over the entrances to the renal arteries but as the wire of the stent is fine occlusion does not occur. The distal end 99 of the prosthesis seals against the wall of one of the iliac arteries and the distal end 155 of the extension prosthesis 104 bears against the wall of the other iliac artery.

The joint 156 between the prosthesis 90 and the extension prosthesis 104 seals because there is a smooth connection between the smooth inner surface of the shorter leg 92 and the smooth outer surface of the proximal end of the extension prosthesis 104.

The size of the prostheses according to this invention may be selected so that there is in effect an interference fit in the sound parts of the vessels to give good sealing onto the inner walls of the vessels. The prosthesis at its widest may range in diameter from 20 mm to 32 mm where it fits into the aorta and from 8 mm to 24 mm where it fits into the iliac arteries.

The embodiment shown in FIG. 15 may have an overall length of from 120 mm to 180 mm not counting the length of the uncovered proximal stent and the extension prosthesis may have a length of from 35 mm to 125 mm and a diameter of from 8 mm to 24 mm. The amount of overlap between the shorter leg of the prosthesis and the proximal end of the extension prosthesis is from 15 mm to 21 mm.

The embodiment shown in FIG. 16 may have an overall length of from 100 mm to 130 mm not counting the length of the uncovered proximal stent. The difference in length between the shorter and longer legs of the bifurcated prosthesis may be 30 mm. The shorter extension prosthesis may have a length of from 65 mm to 125 mm and a diameter of from 8 mm to 24 mm. The amount of overlap between the shorter leg of the prosthesis and the proximal end of the longer extension prosthesis is from 15 mm to 22 mm. The longer extension prosthesis may have a length of from 35 mm to 125 mm and a diameter of from 8 mm to 24 mm. The amount of overlap between the longer leg of the prosthesis and the proximal end of the shorter extension prothesis is from 15 mm to 22 mm.

The embodiment shown in FIG. 17 may have an overall length of from 90 mm to 180 mm not counting the length of the uncovered proximal stent. The prosthesis at its widest may range in diameter from 20 mm to 32 mm where it fits into the aorta and from 8 mm to 24 mm where it fits into one of the iliac arteries.

Throughout this specification unless the context requires otherwise, the words 'comprise' and 'include' and variations such as 'comprising' and 'including' will be understood to imply the inclusion of a stated integer or group of integers but not the exclusion of any other integer or group of integers.

Throughout this specification various indications have been given as to the scope of this invention but the invention is not limited to any one of these but may reside in two or more of these combined together. The examples are given for illustration only and not for limitation.

The invention claimed is:

1. An introducer for the introduction of a prosthesis into a lumen of a patient, the prosthesis comprising a proximal end and a distal end, and at least one self-expanding stent the introducer comprising an external manipulation section which is arranged to remain external of the patient and, a. a proximal attachment device attachable to the proximal end of the prosthesis, b. a distal attachment device attachable to the distal end of the prosthesis, c. each of the proximal and distal attachment devices being attachable to the prosthesis in such a manner that the prosthesis can be held in tension therebetween and that each end of the prosthesis can individually be moved in proximal and distal directions be rotated, and d. proximal releasing means associated with the proximal attachment device and distal releasing means associated with the distal attachment device for enabling selective releasing of the proximal and distal ends of the prosthesis, and e. a proximal trigger wire extending from the proximal attachment device to the manipulation section, the proximal trigger wire activating the proximal releasing means.

2. An introducer as in claim 1 wherein the proximal attachment device has a long flexible extension on its proximal end to facilitate insertion of the introducer into a body lumen and its advancement along the lumen.

3. An introducer as in claim 2 wherein the proximal attachment device is mounted on a flexible thin walled tube which extends in a distal direction from the proximal attachment device to the external manipulation section.

4. An introducer as in claim 3 wherein the thin walled metal tube includes fluid connection means external of the patient to enable the introduction of a medical reagent therethrough.

5. An introducer as in claim 4 wherein the long flexible extension includes a hollow tube therethrough in fluid communication with the thin walled metal tube and a plurality of side holes to enable dispersion of the medical reagent proximal of the prosthesis.

6. An introducer as in claim 3 wherein the distal attachment device is mounted on a flexible thick walled tube and the thick walled tube is coaxial on the thin walled tube and extending in a distal direction to the external manipulation section and mounted such that the respective tubes can be moved together or independently.

7. An introducer as in claim 6 including a haemostatic seal between the thin walled tube and the thick walled tube in the manipulation section.

8. An introducer as in claim 7 including means to introduce a medical reagent into an annular space defined between the thin walled tube and the thick walled tube.

9. An introducer as in claim 6 including an external sheath extendable from external of the patient to cover and compress the prosthesis during insertion of the introducer into a patient and movable longitudinally from outside the patient to expose the prosthesis.

10. An introducer as in claim 9 wherein the external sheath is coaxial with and in a sliding fit on the thick walled tube.

11. An introducer as in claim 10 wherein the external sheath has a proximal end which is tapered and smoothed to present a low resistance to advancement of the introducer during insertion.

12. An introducer as in claim 9 wherein the proximal end of the external sheath has a tight fit on to the proximal attachment device.

13. An introducer as in claim 9 wherein the distal attachment device is of a streamlined shape and is arranged to be advanced to the proximal attachment device whereby to allow smooth retrieval through the released prosthesis and into the external sheath for removal from a patient.

14. An introducer as in claim 1 including a distal trigger wire extending from the distal attachment device to the manipulation section, the distal trigger wire activating the distal releasing means.

15. An introducer as in claim 14 including an external release mechanism on the manipulation section for each of the proximal trigger wire and distal trigger wire, the external release mechanism arranged to prevent accidental release of the trigger wires.

16. An introducer as in claim 15 including a haemostatic seal around the respective trigger wires in the manipulation section.

17. An introducer as in claim 1 wherein the prosthesis is a bifurcated prosthesis.

18. An introducer as in claim 1 wherein the lumen of the patient is an aorta and the prosthesis is adapted to repair an aortic aneurism.

* * * * *